(12) United States Patent
Davelaar

(10) Patent No.: US 6,348,197 B1
(45) Date of Patent: Feb. 19, 2002

(54) IN OVO VACCINATION AGAINST NEWCASTLE DISEASE

(75) Inventor: Frans Gerrit Davelaar, Eg Putten (NL)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/319,481

(22) PCT Filed: Dec. 16, 1997

(86) PCT No.: PCT/EP97/07066

§ 371 Date: Jul. 23, 1999

§ 102(e) Date: Jul. 23, 1999

(87) PCT Pub. No.: WO98/26800

PCT Pub. Date: Jun. 25, 1998

(30) Foreign Application Priority Data

Dec. 17, 1996 (GB) ............................................ 96203572

(51) Int. Cl.$^7$ ................................................ A61K 39/17
(52) U.S. Cl. .................................... 424/214.1; 423/93.6
(58) Field of Search ........................... 424/214.1, 184.1, 424/204.1, 211.1, 93.1, 93.6

(56) References Cited

U.S. PATENT DOCUMENTS 5,149,530 A * 9/1992 van Wiltenburg
5,427,791 A * 6/1995 Ahmad et al.

* cited by examiner

*Primary Examiner*—Patricia A. Duffy
(74) *Attorney, Agent, or Firm*—Adley Mandel; John Levis

(57) ABSTRACT

The present invention is concerned with a vaccine for in ovo vaccination of poultry against Newcastle Disease Infections. This vaccine contains Newcastle Disease Viruses of the strain with the internal indication NDW, deposited at CNCM (Institut Pasteur) under number I-781.

4 Claims, No Drawings

IN OVO VACCINATION AGAINST NEWCASTLE DISEASE

The present invention is concerned with a vaccine suitable for in ovo vaccination against Newcastle Disease infection, with the use of a Newcastle Disease Virus strain in the preparation of such a vaccine, as well as with the protection of poultry against Newcastle Disease infection by in ovo vaccination with a vaccine containing a Newcastle Disease virus train.

In ovo vaccination of virus-containing vaccines was extensively described by Sharma et al. (U.S. Pat. No. 4,458,630). In particular it teaches that live Marek's disease virus can be injected into amniotic fluid within the egg, whereafter the embryo is infected and the vaccine virus replicates to a high titer which induces the formation of protective antibodies in the treated embryo. (Sharma; Avian Diseases 29, 1155, 1167–68 (1985).

In U.S. Pat. No. 5,427,791 Ahmad et al. describe the embryonal vaccination against Newcastle Disease. Herein, in order to provide for a non-pathogenic attenuation of the live Newcastle Disease virus (strain NDV-B 1), the viruses were modified through use of ethyl methane sulfonate (EMS).

A disadvantage of this type of modification is the fact that EMS is a mutagen and that the vaccine is suspected to act as a mutagen as well, which is undesirable for regular administration of the vaccine. On the other hand, untreated NDV-B 1 cannot be applied for in ovo vaccination as almost all of the embryos will die upon injection of the eggs with this unmodified virus.

Furthermore, it has been found that the margin between minimum effective dose and the maximum dose for safety for these modified viruses is less than 10 (hence less than log1). For practical purposes and in view of the errors as a result of production and due to losses during storage, this margin is too small.

Surprisingly it has been found that a vaccine preparation containing Newcastle Disease viruses of the strain NDW is particularly suited for in ovo application. Hence the present invention is concerned with the use of Newcastle Disease virus of the strain NDW in the in ovo vaccination of poultry. As a further embodiment the invention is concerned with the use of Newcastle Disease virus of the strain NDW in the preparation of a vaccine suitable for in ovo administration poultry.

Samples of the Newcastle Disease virus strain NDW were deposited at CNCM of Institut Pasteur under No 781. See EP 351908.

Advantageously, the NDW strain is administered in an amount of between $10^{-1}$ and $10^3$ and more in particular in an amount between $10^{-0.7}$ and $10^{2.2}$ per egg.

For obtaining the best results in immunisation it was found that the NDW containing vaccine can be administered in ovo at between 17 and 19 days of incubation, preferably at 18 days of incubation.

EXAMPLE 1

Preparation of NDW Vaccine for In Ovo Administration

A Working Seed Virus stock was prepared from a Master Seed Virus (deposited at CNMCM (Collection Nationale de Cultures de Microorganismes), Institut Pasteur at 25Rue du Doctor Roux 75724 PARIS CEDEX 15 under No I-781 on July 12, 1988) by inoculation into the allantoic cavity of embryonated SPF chicken eggs.

In the same way the vaccine is produced by inoculation of Working Seed Virus into the allantoic cavity of embryonated SPF eggs. After incubation the allantoic fluid containing the vaccine virus is harvested. The allantoic fluid is diluted and frozen and stored at −50° C.

Before filling the allantoic fluid is thawed, further diluted until the required concentration of vaccine virus, mixed with stabiliser, filled into vials and freeze-dried.

EXAMPLE 2

The Safety of the In Ovo NDW Vaccine in SPF Eggs

SPF eggs were vaccinated at 18 days of incubation in the amnion by the method described by Sharma and Burmester (Avian Diseases 26 (1), 134–149) with the vaccine described in Example 1.

Six groups of eggs were vaccinated according to the scheme outlined in the following Table.

TABLE 1

Safety of in ovo vaccination of SPF eggs with NDW vaccine

| Group | Vaccine dose (in $EID_{50}$) | Number of Eggs | Percentage hatch |
|---|---|---|---|
| 1 | $10^{2.2}$ | 25 | 76 |
| 2 | $10^{1.2}$ | 25 | 84 |
| 3 | $10^{0.2}$ | 25 | 84 |
| 4 | $10^{-0.8}$ | 25 | 88 |
| 5 | $10^{-1.8}$ | 25 | 92 |
| 6 | controls | 25 | 96 |

Conclusion: In ovo vaccination of SPF eggs at 18 days of embryonal development with NDW vaccine is safe with a maximum dose of between $10^{1.2}$ and $10^{2.2}$ $EID_{50}$ per egg.

EXAMPLE 3

The Safety of the In Ovo NDW Vaccine in Commercial Broiler Eggs with Maternal Antibodies Commercial broiler eggs having maternal antibodies were vaccinated at 18 days of incubation in the amnion by the method described by Sharma and Burmester (Avian Diseases 26 (1), 134–149) with the vaccine described in Example 1.

Eight groups of eggs were vaccinated according to the scheme outlined in the following Table.

TABLE 2

Safety of in ovo vaccination of commercial broiler eggs with NDW vaccine

| Group | Vaccine dose (in $EID_{50}$) | Number of Eggs | Percentage hatch |
|---|---|---|---|
| 1 | $10^6$ | 50 | 68 |
| 2 | $10^5$ | 50 | 70 |
| 3 | $10^4$ | 50 | 74 |
| 4 | $10^3$ | 50 | 76 |
| 5 | $10^2$ | 50 | 91 |
| 6 | $10^1$ | 50 | 84 |
| 7 | $10^0$ | 50 | 96 |
| 8 | controls | 50 | 88 |

Conclusion: In ovo vaccination of broiler eggs with maternal antibodies is safe (no effect on hatching) up to a dose of at least $10^2$ $EID_{50}$ per egg.

EXAMPLE 4

Efficacy of In Ovo Vaccination of SPF Eggs with NDW Vaccine

The efficacy of NDV vaccine prepared according to Example 1 was examined in SPF eggs.

Parameters for the protection were the antibody response after vaccination (haemagglutination inhibition test=HI test) and percentage of mortality after challenge. The challenge virus was the strain Hertz 33/56 of Newcastle Disease Virus, with was administered to each of the chickens in an amount of $10^{5.0}$ $EID_{50}$.

Five groups of eggs were vaccinated according to the scheme outlined in the table below:

TABLE 3

Efficacy of in ovo vaccination of SPF eggs.

| Group | Vaccine Dose (in $EID_{50}$) | HI titer (in $^2$log) at weeks 4 | 6 | Percentage mortality after challenge at 4 weeks |
|---|---|---|---|---|
| 1 | $10^{1.7}$ | 4.6 | nd | 0 |
| 2 | $10^{1.0}$ | 5.1 | 5.7 | 0 |
| 3 | $10^{0.0}$ | 3.6 | 3.3 | 0 |
| 4 | $10^{-0.7}$ | 3.3 | 3.2 | 11 |
| 5 | control | 1.0 | 1.0 | 100 |

Conclusion: In ovo vaccination of SPF eggs at 18 days of embryonal development with NDV vaccine is effective. A vaccine dose of about $10^{-0.7}$ per egg is the minimal effective dose for in ovo NDV vaccination.

EXAMPLE 5

Efficacy of In Ovo Vaccination with NDW Vaccine of Commercial Broiler Eggs with Maternal Antibodies The efficacy of the NDV vaccine prepared according to Example 1 was examined in commercial broiler eggs with maternal antibodies (HI titer of 5.1 at one day of age).

Parameters for the protection were the antibody response after vaccination (HI test) and percentage of mortality after challenge. The challenge virus was the strain Hertz 33/56 of Newcastle Disease Virus, which was administered to each of the chickens in an amount of $10^{5.0}$ $EID_{50}$.

Three groups of eggs were vaccinated according to the scheme outlined in the table below:

TABLE 4

Efficacy of in ovo vaccination in commercial broiler eggs

| Group | Vaccine Dose (in $EID_{50}$) | HI titer (in $^2$log) at 3 weeks of age | Percentage of mortality after challenge at 3 weeks of age |
|---|---|---|---|
| 1 | $10^2$ | 3.9 | 0 |
| 2 | $10^{-1}$ | 2.4 | 0 |
| 3 | control | 1.0 | 100 |

Conclusion: In ovo vaccination with NDV vaccine of commercial broiler eggs at 18 days of embryonal development is effective. This is not influenced by the presence of maternal antibodies.

What is claimed is:

1. A method for in ovo vaccination which comprises adding the viruses of Newcastle Disease Virus strain NDW, deposited at CNCM (Institut Pasteur) under number I-781, in a dosage amount of between about $10^{-1}$ $EID_{50}$ and $10^3$ $EID_{50}$ per egg without ethyl methane sulfonate.

2. A method for in ovo vaccination which comprises adding the viruses of Newcastle Disease Virus strain NDW, deposited at CNCM (Institut Pasteur) under number I-781, in a dosage amount of between $10^{-0.7}$ $EID_{50}$ and $10^{2.2}$ $EID_{50}$ per egg without ethyl methane sulfonate.

3. A method for preventing or treating Newcastle Disease infections in poultry comprising in ovo administration of a vaccine comprising a virus having the immunogenic characteristics of the strain NDW an example of which is deposited at CNCM (Institut Pasteur) under number I-781, wherein said vaccine is administered without ethyl methane sulfonate.

4. The method according to claim 1, wherein said vaccine is administered to the allantoic cavity of embryonated SPF chicken eggs.

* * * * *